United States Patent [19]
Mullon et al.

[11] Patent Number: 5,741,334
[45] Date of Patent: Apr. 21, 1998

[54] ARTIFICIAL PANCREATIC PERFUSION DEVICE

[75] Inventors: Claudy Jean Paul Mullon, Framingham; Karen E. Dunleavy, Billerica, both of Mass.

[73] Assignee: Circe Biomedical, Inc., Lexington, Mass.

[21] Appl. No.: 732,146

[22] Filed: Oct. 16, 1996

Related U.S. Application Data

[63] Continuation of Ser. No. 488,033, Jun. 7, 1995, abandoned.
[51] Int. Cl.[6] ............................................. A61F 2/04
[52] U.S. Cl. ........................ 623/12; 623/11; 424/424
[58] Field of Search ........................... 623/1, 11, 12; 604/4; 210/192, 321.78, 321.87; 424/424, 423, 422; 435/283.1, 284.1

[56] References Cited

U.S. PATENT DOCUMENTS

| | | | |
|---|---|---|---|
| 4,378,016 | 3/1983 | Loeb | 424/424 |
| 5,002,661 | 3/1991 | Chick et al. | 210/192 |

*Primary Examiner*—John G. Weiss
*Assistant Examiner*—Francis K. Cuddihy
*Attorney, Agent, or Firm*—Margit Maus

[57] ABSTRACT

An artifical pancreatic perfusion device comprising a hollow fiber having a porosity ranging from about 25 Kd to about 200 Kd. The hollow fiber has one end connected to a blood vessel for receiving blood and a second end connected to a blood vessel for returning said blood. Islets of Langerhans surround the hollow fiber. The hollow fiber and islets are surrounded by a housing comprising a semipermeable membrane having a pore size small enough to offer protection to the islets and host from immune reactive substances. Further disclosed is a method for providing and regulating insulin to insulin deficient individuals.

21 Claims, 2 Drawing Sheets

ARTIFICIAL PANCREATIC PERFUSION DEVICE

CROSS REFERENCE TO RELATED APPLICATION

This application is a continuation of applicant's application Ser. No. 08/488,033 filed Jun. 7, 1995, now abandoned.

BACKGROUND OF THE INVENTION

The present invention relates in general to an artifical pancreas device and more specifically to a combined diffusion/ultrafiltration artificial pancreas.

Epidemiological studies estimate the incidence of diabetes to be between 2–6% of the population. Given the lack of a cure, treatment is longterm and as such drains social resources. In addition, the disease brings on secondary complications which are progressively more and more debilitating. One such complication is decreased vascular flow.

A recent study demonstrated a cause and effect relationship between glucose control and microvascular complications in patients with diabetes mellitus. Reichard, M. D. et al, *The Effect of Long-Term Intensified Insulin Treatment on the Development of Microvascular Complications of Diabetes Mellitus*, New England Journal of Medicine, Jul. 29, 1993. The investigators noted a statistically significant decrease in retinopathy, nephropathy, and neuropathy. Thus there would be many benefits to developing an artificial pancreas which could control the level of glucose so as to decrease the progressive complications of the disease.

Many modalities are currently available to replace the impaired pancreatic beta cell function in diabetes mellitus patients. The electromechanical modality utilizes insulin delivery systems which release insulin in response to blood glucose levels which are continuously measured via a glucose sensor. Difficulties with the sensors led to the development of programmed insulin delivery via a continuous perfusion pump. This approach however also falls short of the in vivo regulation i.e. the regulation of insulin secretion by glucose and its modulation by several humoral, hormonal and neuronal factors. In other words the inherent consistency of programming is not natural.

Pancreas transplants are another approach. Unfortunately, this approach suffers from immune rejections and limited availability of transplantable tissue.

To overcome immune rejection, bioartificial systems were developed. These systems separate the transplanted tissue from the diabetic patient by an artificial barrier which diminishes immune rejection. It accomplishes this by having a selectively permeable barrier which is permeable to glucose and insulin but not to immunoglobulins and immunocytes. Artificial pancreas devices work is based on the transfer through the membrane of a glycemic signal from blood to the islet cells, and from insulin from the islet cells to the recipient. Since the mechanics of glucose and insulin transfer across the membrane involve diffusion and convection, devices are divided among diffusion mechanisms and convection mechanisms or a combination of both.

In general, the transfer of a substance from one compartment to the other across a membrane can be achieved either by diffusion, dialysis, or by convection, ultrafiltration or both. Diffusion represents the transfer of the substance itself without transfer of the solvent. Convection, in contrast, involves the transfer of the solvent and any molecules dissolved therein as long as they are smaller than the pores of the membrane.

The first diffusion based artificial pancreas comprised a chamber consisting of two discs of membrane tightened together at the periphery with transplanted tissue placed in between said membranes. This device although an admirable first attempt suffered many disadvantages. First the glucose and insulin transfer was so slow that it was impossible to regulate blood glucose on a minute by minute basis. Second, the membrane became covered by fibrosis on the side in contact with the recipient tissues. The fibrosis led to decreased oxygen and nutrient transfer to the islet cells. Third, islet cells only survived for a few weeks after transplantation. To combat these disadvantages, the prior art placed pancreatic tissue inside a hollow fiber. Specifically the device comprised pancreatic cells placed inside Amicon 50K hollow fibers. These fibers were sealed at the ends and implanted into the peritoneal cavity of diabetic Chinese hamsters. Blood glucose levels normalized and glycosuria was suppressed for several months.

To increase the transfer of nutrients and the kinetics of the transmission of the glucose signal to the islets, the prior art thought to reduce the volume of the islet compartment by individually microencapsulating the islet cells. These devices are immune protected and the cells survive for a long term. Moreover, they maintain rapid in vitro glucose-insulin kinetics.

A still further device is a diffusion vascular hybrid pancreatic device. In this device, blood is circulated from the recipient through one or several hollow fibers while the islets are placed outside the membrane within a rigid jacket. This type of device can be made part of a vascular shunt. Both animal and human studies performed on such devices showed a correction of hyperglycemia within 5 hours without overshoot hypoglycemia. Unfortunately however, most experiments were of short duration because of thrombosis inside the device or because of bleeding following the heparinization administered to combat the clotting. Thus the device is not biocompatible.

To combat the limited ability to achieve rapid glucose insulin kinetics, alternative systems using the other kind of molecular movement were designed. Namely, convection or ultrafiltration devices. Blood was circulated through a hemofilter and perifused islets placed in a millipore chamber, said blood ultimately being reinfused into a peripheral vein. This system used flat polyacrylonitrile membranes with a particular molecular cut off, hemocompatibility, and high ultrafiltration coefficient. Short term experiments were successful. However, the system has the drawback of requiring a large membrane surface area to produce enough ultrafiltrate.

Lastly, the prior art has produced a combined diffusion/ ultrafiltration artificial pancreas. This system relies on the inherent ultra filtration flux present in diffusion hollow fiber systems. More specifically, a minute ultrafiltration-reabsorption cycle is present in the closed islet compartment surrounding the hollow fibers of the vascular diffusion hybrid pancreatic devices. Indeed, at the inlet of the fiber, the transmembrane pressure produces an ultra filtration flux from blood to islets, and at the fiber outlet, the hydrostatic pressure inside the fibers drops, and the transmembrane pressure produces reabsorption of fluid from the islet compartment to blood. This system comprises a chamber consisting of two flat polyacrylonitrile membranes, with blood circulating successively above the first and below the second membrane in the reverse direction. Islet cells are introduced into the chamber.

Test results showed that insulin was released within 5 minutes in response to glucose. Advantageously, in this device response time is independent of the membrane surface making it attractive for implantation. In addition, insulin release from the device is proportional to the number of islets, suggesting that the beta function is not suppressed by insulin, which is continuously carried away across the adjacent part of the membrane by the ultrafiltration flux. In sum, the prior art combined the ultrafiltration flux inherent in capillary units in a convection device.

While all the aforementioned prior art attempts to create an artificial pancreas are admirable, none are completely satisfactory. It is thus a primary objective of the present invention to improve upon the prior art by providing for a device which combines the attributes of a diffusion and ultrafiltration device. More specifically a device which not only relies on an inherent ultrafiltration flux but advantageously provides for an artifical pancreas device which employs both convective and diffusion membrane transport.

A further objective of the present invention is to provide for an implantable device which is biocompatible.

A still further objective of the present invention is to provide for an implantable device which is nontoxic.

A still further objective of the present invention is to provide for an implantable device which immunoisolates the transplanted tissues.

SUMMARY OF THE INVENTION

The aforementioned objectives are met by the present invention providing for an artifical pancreas device which employs both convective and diffusion membrane transport. More specifically, a novel artificial pancreas device comprising a hollow fiber surrounded by pancreatic islet cells, both fiber and cells encased in a housing having a semipermeable membrane.

DETAILED DESCRIPTION OF THE INVENTION

As previously mentioned the present invention is an improvement of applicants' earlier inventions descibed in U.S. Pat. Nos. 5,002,661, 5,116,493 and 5,116,494, hereby incorporated by reference. The improvement rests within the semipermeable nature of the housing. Semipermeability adds an additional membrane transfer mechanism, namely convection. Convection transport allows fitted to perfuse the islet chamber which improves the transport of insulin out of the device and glucose into the device as well as the transmission of the glucose signal to the islets. In sum the device offers a more sensitive glucose control mechanism.

In use the novel device may be implanted in the peritoneal cavity of an animal or human. As such secreted insulin may in addition to entering the peripheral vascular system, enter the portal system and provide insulin to the liver directly. In contrast, the prior art vascular devices which are connected to peripheral arteries and veins, deliver insulin only peripherally which often results in peripheral hyperinsulemia because one needs to overshoot peripherally in order to obtain optimal results centrally.

Still further, the novel device allows for more direct signals and response by prividing for convection and ultrafiltration simultaneously. As per the aforementioned Reichard article, the more sensitive the control the less the complications associated with diabetes mellitus.

Specifically the present invention comprises an artificial pancreatic perfusion device comprising a hollow fiber having a porosity or molecular weight cut off ranging from about 20,000 Dalton to about 200,000 Dalton. Said hollow fiber having one end connected to a blood vessel for receiving blood and a second end connected to a blood vessel for returning said blood to the patient. Islets of Langerhans are seeded around said hollow fiber. Said fiber and islets are enclosed in a semipermeable housing having a pore size small enough to offer protection to the islets and host from immune reactive substances.

In use the novel pancreatic perfusion device allows for ultrafiltration and convection transport. The hollow fiber providing for ultrafiltration and the semipermeable housing providing for convection. Thus blood flow through the hollow fiber assures a steady supply of nutrients to the islets while fluid perfuses from the islet chamber into the peritoneal cavity and/or the peritoneal cavity into the islet chamber thereby improving insulin transport and islet response. In one embodiment of the present invention, the device is implanted in the peritoneal cavity. Thus insulin would be secreted into blood and delivered systemically and insulin would be secreted into the portal system thereby delivering insulin directly to the liver. The advantage of such a dual secretion pathways ensures a better insulin/glucose control mechanism which in turn results in decreased side complications.

Figure 1:
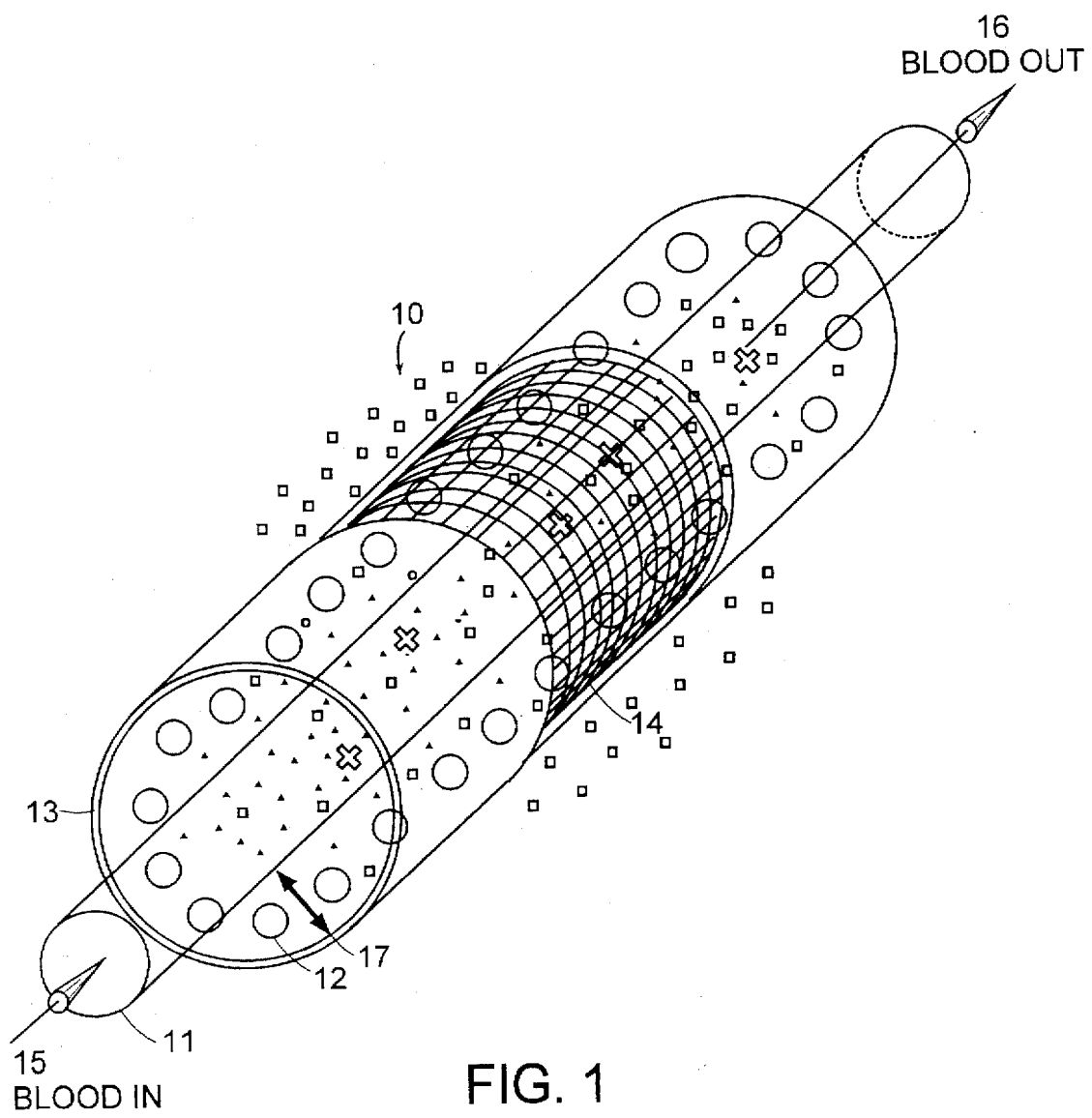
FIG. 1 is a schematic view of one embodiment of the invention.

FIG. 1 offers a schematic view of a general embodiment of the invention. Pancreatic perfusion device 10, comprises a hollow fiber 11, islets of Langerhans 12, and a housing 13, comprising a semipermeable membrane 14. Blood enters at inlet end, 15, flows through the fiber and exits at outlet end 16.

By way of illustration and not limitation hollow fiber 11, may be manufactured from polyacrylonitrile, polysulfone, polyvinylchloride, porous tetrafluoroethylene or a copolymer of any of the aforementioned, etc. The polyacrylonitrile polyvinylchloride copolymer being most preferred. The pore size of hollow fiber 11 is restricted to that which prevents an autoimmune response. More specifically, molecular cut offs ranging from about 25,000 Daltons to about 200,000 are contemplated. 80,000 Dalton being preferred.

The exact dimensions of fiber 11, are dictated by the amount of insulin to be produced. A surface area from about 50 to about 100 cm squared is required to sustain 500,000 islets of Langerhans. Since surface area is the product of the length of the fiber, the inner diameter of the fiber and 11, the present invention contemplates lengths from about 30 to about 80 cm, and diameters from about 5 mm to about 10 mm.

Housing 13 may be manufactured of any of the known biocompatible materials including but not limited to acrylics, polycarbonate, polysulfone, etc. Acrylic being most preferred. Semipermeable membrane 14, may be manufactured from any of the known tissue compatible materials. By way of illustration and not limitation mention may be made of the polyacrylonitrile, polysulfone, polyvinylchloride, porous tetrafluoroethylene or a copolymer of any of the aforementioned, etc. The polyacrylonitrile polyvinylchloride copolymer being most preferred.

By semipermeable we mean having a pore size small enough to offer protection to the islets and host from immune reactive substances. More quantitatively speaking, having a molecular weight cut off ranging from about 25,000

Daltons to about 200,000 Daltons. 80,000 Daltons being most preferred. Semipermeable membrane 14, may comprise all or part of housing 13. Dimensionally speaking, housing 13 may be from about 1 cm to about 10 cm in length and from about 1 cm to about 10 cm in diameter. In other words it may take on any dimension within this range so long as the surface area for the islets is met.

Housing 13, may take on any shape provided that hollow fiber 11 is enclosed in its entirety and the housing provides for a stable space, islet chamber 17, between fiber 11, and the interior walls of housing 13 for the seeding of the islets of Langerhans. Moreover to ensure maximum diffusion of the control signals for insulin secretion, the present invention contemplates distances ranging from about 250 um to about 4 mm between hollow fiber 11 and the interior walls of housing 13. Thus in FIG. 1 housing 13, is essentially cylindrical whereas in FIG. 2 housing 13, is annular.

Figure 2:
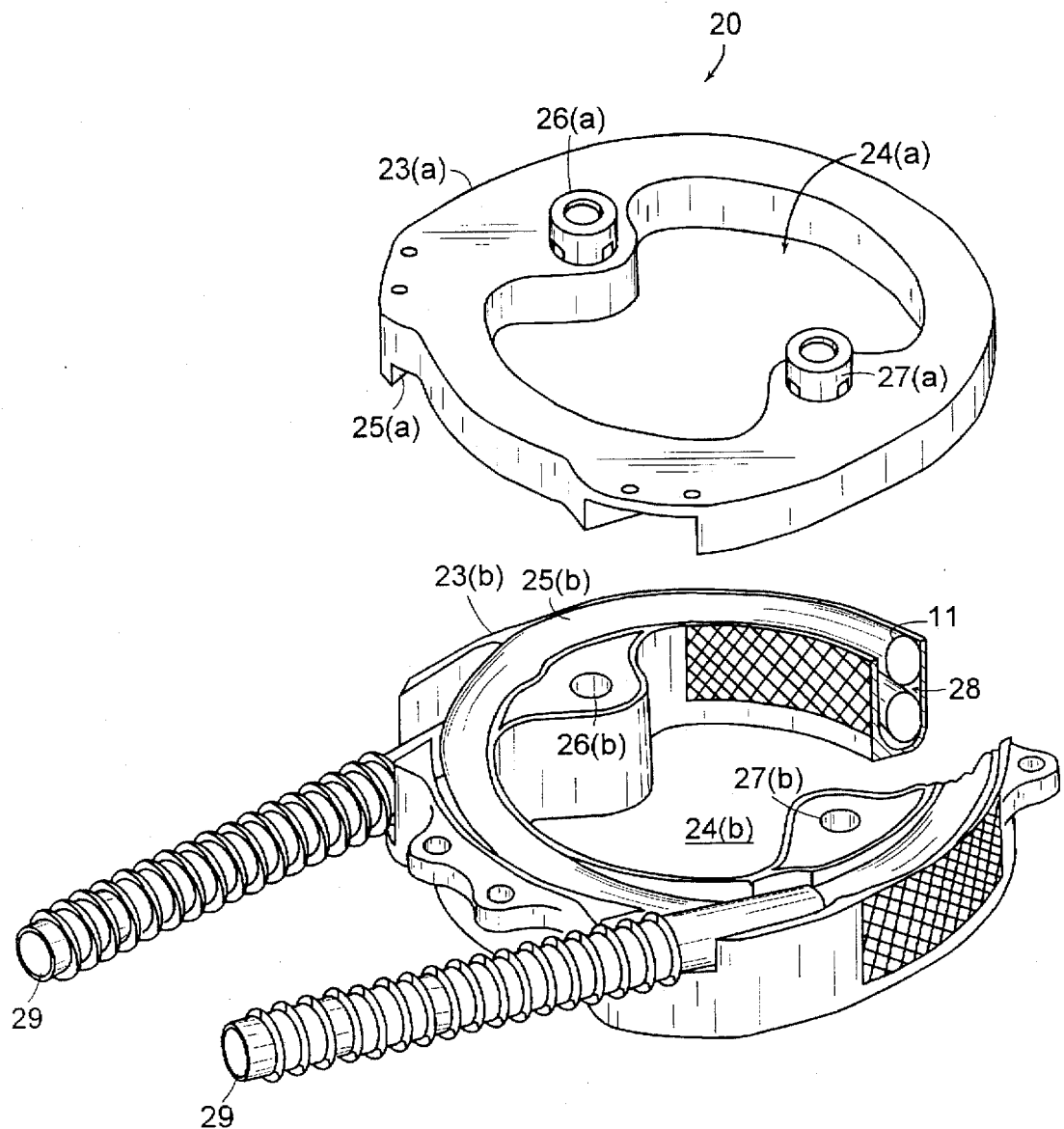
FIG. 2 is an exploded view of a second embodiment of the invention.

In FIG. 2 housing 23 is annular and comprises a bottom half 23(b) and a top half 23(a). 23(b) comprises a FIG. 8 central cavity 24(b), an inner circumferential groove 25(b), and two injection ports 26(b) and 27(b).

In the annular housing embodiment, hollow fiber 11 is coiled into one or more loops about a longitudinal axis inside housing 23 in groove 25(b) and 25(a). More specifically, hollow fiber 11 may be up to 150 cm in length and up to 7½ times coiled. Ends 15 and 16 may be attached to connecting means. By way of illustration and not limitation mention may be made of polyurethane, porous tetrafluoroethylene, polyester, etc. connecting means. In FIG. 2 vascular graft 29 is illustrated. Said grafts may or may not protrude from the housing.

23(a) comprises a central FIG. 8 cavity, 24(a), injection ports 26(a) and 27(a), and an inner grove 25(a), so as to match bottom half housing 23(b) upon superposition. Top half housing 23(a) is superimposed upon bottom half housing 23(b) to provide a hermetic seal via chemical or mechanical means. An illustrative mechanical means is welding and more specifically ultrasonic and radiofrequency welding.

Islets of Langerhans are seeded circumferentially along hollow fiber 11 in islet chamber 28. More specifically the islets are distributed so as to fill the spaces between loops of hollow fiber 11 and the inner wall of housing 23. To ensure even distribution, each loop of hollow fiber 11 may be spaced apart from another loop by spacer(s) 31 (not shown).

Islets are introduced into chamber 28, via injection ports 26 and 27. More specifically they are introduced in a first syringe at port 27(a). A second but empty syringe is simultaneously fitted to port 26(a), where air is sucked into the syringe thereby creating a flow between port 26, islet chamber 28 and port 27 which results in the islets being discharged from the first syringe and deposited in islet chamber 28. In other words, the islets are drawn through one port 27, by negative pressure created at the other port 26. Notably, while a negative pressure system is herein described, any injection means is contemplated including but not limited to negative and positive pressures.

Ports 26 and 27 may be manufactured of any biocompatible material including but not limited to silicone, polyurethane, epoxy, acrylic etc. Silicone being most preferred. To prevent leakage of islets, ports 26 and 27 may be sealed via an injectable or piercable material such as rubber, cork, silicone polyurethane, etc. In other words, port 26 and 27 may only be open when a syringe is in place. In other words, the ports are resealable, self-sealing or otherwise covered. If ports 26 and 27 are not sealed, then they may be outfitted with covers 36 and 37 (not shown). Once the islets are injected, covers 36 and 37 may be positioned to close ports 26 and 27 to prevent islet leakage. In other words, these ports may be self-sealing or resealable. Covers 36 and 37 may be manufactured from any known biocompatible material including but not limited to silicone, acrylic, etc. Silicone being most preferred.

Housing 23 may also comprise one or more attachment sites for anchoring device 20 to the patient. By way of illustration and not limitation suitable attachment means are sutures, staples, etc.

Islets of Langerhans 12, may be harvested from humans and any number of animals including but not limited to pigs, dogs, rats, calves, etc. Pig islets being most preferred. The particular harvesting process comprises no part of this invention and as such may comprise any one of the well known techniques. In general terms islets are harvested from pig pancreata using a collagenase digestion process followed by a ficoll gradient method to separate the beta cells or islets from the other tissue.

The islets of Langerhans are seeded in the artificial pancreas device in a manner so as to be evenly distributed around hollow fiber 11. The current invention is not restricted to any particular culturing and/or seeding techniques. Applicant contemplates use of any of the currently available seeding and culturing techniques. Regarding media, applicant contemplates both protein and protein free media, yet prefers media with protein and specifically with fetal calf serum. Most preferred are islets cultured in MEM (Minimum Essential Media). This technique is specifically described in U.S. Pat. No. 5,002,666, hereby incorporated by reference.

Once cultured, the islets are spun down and the supernatant is removed, and the islets are thereafter mixed into the chosen matrix. For a solid agar gel matrix, a 2 wt % agar solution is prepared, heated and mixed until completely dissolved. Thereafter equal amounts of the 2% agar solution and appropriate media solution are heated and mixed. When the 1% agar solution reaches an appropriate temperature, namely from about 40 degrees Celsius to about 50 degrees Celsius, preferably 40-43 degrees Celsius, the islets are added.

When a bead type matrix is contemplated, the isolated islets are mixed in the media of choice and formed in appropriate manner. The present invention is not limited to any particular media or process of bead manufacture but contemplates any of the currently known ones. By way of illustration and not limitation mention may be made of alginate based, agar based or agarose media and emulsification in oil, ionic gelation and subsequent extrusion techniques may be mentioned for processes of bead manufacture.

No matter what culturing media or matrix is chosen, for seeding, the liquid agar or bead suspension is preferrably placed in a syringe having a bore needle ranging in diameter from about 20 to about 18 g. The syringe is used to pierce one of the device ports while the other port remains open to function as a vent. In this manner the islets are injected into the device chamber. Once the device is seeded, the device is maintained on ice from about 0.5 to about 3.5 degrees Celsius until surgery.

In order to ensure even distribution the islets may be suspended in any of the known matrices or supporting materials which include but are not limited to, gels, semi-gel, temperature sensitive matrices, slurries, etc. In particular mention may be made of the matrix described in U.S. Pat.

No. 5,116,494 issued to the present assignee and hereby incorporated by reference. More specifically, the islets are embedded in beads. Any matrix is contemplated so long as it maintains cell viability.

In use the novel pancreatic perfusion device is connected at inlet end 15 and outlet end 16, to a blood vessel in a manner that provides for a smooth and continuous flow of blood through the novel device. By blood vessels we mean both arteries and veins. More specifically, any vessel which will remain patent is contemplated. Quantitatively speaking, any vessel with a diameter ranging from about 3 to about 10 mm is contemplated, vessels from about 4 to about 8 mm being prefered. The manner of connecting the novel device to said arteries or veins comprises no part of this invention. Any number of known connecting means, illustrative ones being sutures and grafts, may be used so long as they are biocompatible, non-absorbable and provide for a smooth and continuous flow of blood. By way of illustration and not limitation, mention may be made of porous tetrafluoroethylene, polyester, etc. Porous tetrafluoroethylene being most preferred.

In addition, the novel pancreatic perfusion device may be implanted into a body cavity such as the peritoneal cavity or abdominal, etc. When implanted into the peritoneal cavity the device may be anastomosed to the iliac artery and vein, the iliac artery and femoral vein, or artery to artery. Physiologically speaking, however, an artery/vein connection is preferred. When connected in this manner the device functions as an arterio-venous shunt.

Since certain changes may be made without departing from the scope of the invention as described herein, it is intended that all matter described in the foregoing specification, including the examples, shall be interpreted as illustrative and not in a limiting sense.

We claim:

1. An artifical pancreatic perfusion device, comprising:
   a. a hollow fiber having a porosity ranging from about 25 Kd to about 200 Kd; said hollow fiber having a first end adapted to be connected to a blood vessel for receiving blood and a second end adapted to be connected to a blood vessel for returning blood;
   b. islets of Langerhans surrounding said hollow fiber, wherein the fiber provides for a directly continuous blood flow between said receiving blood vessel and said returning blood vessel; and
   c. a housing for said hollow fiber and islets, comprised in whole or in part by a semipermeable membrane; said housing having a pore size small enough to offer protection to the islets and host from immune reactive substances.

2. The artificial pancreatic perfusion device of claim 1, wherein the semipermeable membrane has a molecular weight cut off from about 25 Kd to about 200 Kd.

3. The artificial pancreatic perfusion device of claim 1, wherein the semipermeable membrane comprises part of the housing.

4. The artificial pancreatic perfusion device of claim 1, wherein the semipermeable membrane comprises all of the housing.

5. The artificial pancreatic perfusion device of claim 1, wherein said islets of Langerhans are suspended in a matrix consisting of acrylic polycarbonate, polysulphone, or polyurethane.

6. The artificial pancreatic perfusion device of claim 1, wherein an inner surface area of the hollow fiber is from about 50 cm squared to about 100 cm squared.

7. The artificial pancreatic perfusion device of claim 5, comprising from about 30K to about $1\times10^9$K islet of Langerhans.

8. The artificial pancreatic perfusion device of claim 1, wherein the housing is cylindrical.

9. The artificial pancreatic perfusion device of claim 1, wherein the housing is annular.

10. A method for providing and regulating insulin to insulin deficient individuals, comprising the steps of:
    a. seeding a device as described in claim 1, with islets of Langerhans;
    b. attaching one end of said device to a blood vessel for receiving blood and attaching the other end to a blood vessel for returning blood to the patient;
    c. circulating blood through said device.

11. A method for providing and regulating insulin to an insulin deficient individual, comprising the steps of:
    a. seeding a device as described in claim 1, with islets of Langerhans;
    b. attaching an inlet end of said device to a blood vessel for receiving blood and attaching an outlet end of said device to a blood vessel for returning blood to an individual;
    c. implanting said device into an individual and circulating blood through said device so that blood circulates through said hollow fiber, and body fluid perfuses through said housing so that insulin is secreted through said hollow fiber as well as through said housing.

12. The articial pancreatic perfusion device described in claim 9, wherein the device is adapted to be attached to a blood vessel for receiving blood and a blood vessel for returning blood via a vascular graft.

13. The articial pancreatic perfusion device described in claim 9, wherein the islets of Langerhans are seeded in a suspension or a gel matrix.

14. The articial pancreatic perfusion device described in claim 12, wherein from about 100,000 to about 2,000,000 islets are seeded.

15. The articial pancreatic perfusion device described in claim 9, wherein the semipermeable membrane has a pore size from about 25 Kd to about 200 Kd.

16. The articial pancreatic perfusion device described in claim 14, wherein the semipermeable membrane comprises part of the housing.

17. The articial pancreatic perfusion device described in claim 14, wherein the semipermeable membrane comprises all of the housing.

18. The method described in claim 14, wherein the housing is cylindrical.

19. The articial pancreatic perfusion device described in claim 14, wherein the housing is annular.

20. The artifical pancreatic perfusion device described in claim 1, wherein the islets of Langerhans are suspended in a liquid, gel, or bead matrix.

21. The artifical pancreatic perfusion device described in claim 20, wherein the islets of Langerhans are suspended in an agar, alginate, or agarose bead matrix.

* * * * *